(12) United States Patent
Blodgett

(10) Patent No.: US 6,829,938 B2
(45) Date of Patent: Dec. 14, 2004

(54) METHOD AND APPARATUS FOR SELECTING TREES FOR HARVEST

(75) Inventor: David W. Blodgett, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/676,640

(22) Filed: Oct. 1, 2003

(65) Prior Publication Data

US 2004/0069064 A1 Apr. 15, 2004

Related U.S. Application Data

(60) Provisional application No. 60/416,062, filed on Oct. 4, 2002.

(51) Int. Cl.[7] .............................................. G01H 13/00
(52) U.S. Cl. ....................................... 73/579; 73/651
(58) Field of Search ........................... 73/579, 651, 602

(56) References Cited

U.S. PATENT DOCUMENTS

| | | | |
|---|---|---|---|
| 3,877,294 A | 4/1975 | Shaw | |
| 4,059,988 A | 11/1977 | Shaw | |
| 4,702,111 A | 10/1987 | Holland | |
| 5,760,308 A | 6/1998 | Beall et al. | |
| 2002/0112542 A1 | 8/2002 | Walker | |

FOREIGN PATENT DOCUMENTS

| | | | |
|---|---|---|---|
| CA | 997052 | | 9/1976 |
| SU | 1718114 | * | 3/1992 |

* cited by examiner

Primary Examiner—Herzon Williams
Assistant Examiner—Nashmiya Fayyaz
(74) Attorney, Agent, or Firm—Albert J. Fasulo, II

(57) ABSTRACT

A method for selecting trees for harvest according to a predetermined criterion is provided which includes at least the steps of applying a vibrative member to the tree, vibrating the vibrative member, determining the resonance properties of the vibrative member, calculating an observed quality factor associated with the vibrative member vibrations, and, comparing the observed quality factor with a predetermined relationship between the quality factor and the tree selection criterion. A portable tree probe, suitable for field use, is also provided.

21 Claims, 3 Drawing Sheets

METHOD AND APPARATUS FOR SELECTING TREES FOR HARVEST

CROSS REFERENCE TO RELATED APPLICATIONS

This application claims priority to U.S. Provisional Application No. 60/416,062, filed Oct. 4, 2002, the contents of which are incorporated herein by reference.

BACKGROUND OF THE INVENTION

1. Field of the Invention

The present invention generally relates to a method and apparatus for testing trees. More particularly, the present invention is directed to a method and apparatus for selecting trees for harvest by testing the material properties of the trees in the field.

2. Description of the Related Art

It is known that it is necessary for lumber companies to test trees in order to determine which ones are to be cut down. For example, mature trees are selected for harvesting, while immature trees are left standing for further growth. One way to accomplish this is by taking a core sample of the tree and sending it to a laboratory to determine the density of the wood, which is related to the maturity of the tree. However, this process in undesirable because it is slow and injures the tree as coring typically produces a hole of from 1 to 3 inches in diameter which extends to the center of the tree. An opening of this size in the tree left by the coring process can provide an entryway into the interior of the tree for tree pathogens such as bacteria, fungi, and insect pests that ultimately cause the tree to rot.

Various methods for testing the material properties of trees in the field are known. For example, U.S. Pat. No. 3,877,294 to Shaw discloses a vibration technique for rot detection in wooden poles and trees. The technique includes applying a mechanical vibrational force at sonic frequencies to, for example, a pole to be tested for rot, and measuring the level of energy emerging from a number of axially spaced points along the length of the pole and comparing the measurements of the emergent energy at the respective points. Shaw teaches that decay induced rot manifests itself as a material of lower density than good quality wood. The less dense material presents a lower impedance and, for a given resonant-like input signal, emergent energy is higher than that passing through good wood.

What is needed, however, is a simple and inexpensive method for determining tree maturity in the field.

SUMMARY OF THE INVENTION

A method for selecting trees in accordance with a predetermined criterion is provided herein. In one embodiment of the present invention, a method for selecting trees is provided comprising applying a vibrative member to the tree, the vibrative member being characterized by mechanical vibration resonance properties; vibrating the vibrative member; determining the resonance properties of the vibrative member; calculating an observed quality factor associated with the vibrative member vibrations; and, comparing the observed quality factor with a predetermined relationship between the quality factor and the tree selection criterion.

Another embodiment of the present invention is a portable tree probe, suitable for field use, comprising (a) a vibrative member having a wood-penetrating end portion with at least one mechanical resonance frequency; (b) means for vibrating the vibrative member at about the resonance frequency of the wood-penetrating end portion; and, (c) means for measuring vibration amplitude across a frequency range sufficient to determine a characteristic Q value.

The method and portable tree probe of the present invention advantageously provide a way for trees to be tested in order to determine if a tree should be harvested, based on its maturity, with minimal damage to the tree. Thus, trees that are not cut down can remain standing for further growth and maturity without suffering from such problems as rotting.

BRIEF DESCRIPTION OF THE DRAWINGS

Various embodiments are described below with reference to the drawings wherein.

DETAILED DESCRIPTION OF THE PREFERRED EMBODIMENT(S)

The method of the present invention employs a probe having a predetermined resonant frequency of mechanical vibration. Resonances can be characterized by a quality factor, or Q. A simple definition of the Q factor is that it is the ratio of the resonance frequency $f_0$ to the frequency 3 dB bandwidth $\Delta f$, or, as set forth in equation I:

$$Q = f_0/(f_2 - f_1) \qquad (I)$$

wherein $f_1$ and $f_2$ are the half power points.

In general, the resonance of a tuning fork depends upon such factors as, for example, the size, shape and materials of its manufacture. When not attached to a tree, the tuning fork has a well defined resonant frequency profile with a high value (typically over 100) for the Q factor. However, when embedded into a tree the Q value will drop because of the damping forces exerted by the tree. These damping forces are related to the viscoelastic properties of the tree, which, in turn, are related to the tree maturity. Accordingly, by measuring the Q value of the embedded tuning fork in a target tree and comparing that value with pre-measured Q values associated with trees of the same type and of predetermined ages, the maturity of the target tree, and hence the suitability for harvesting the tree, can be determined. It should be understood that the viscoelastic property of the tree, and hence the measurement of the Q value, is independent of the size and shape of the tree, as well as the surrounding soil type and conditions.

Figure 1:
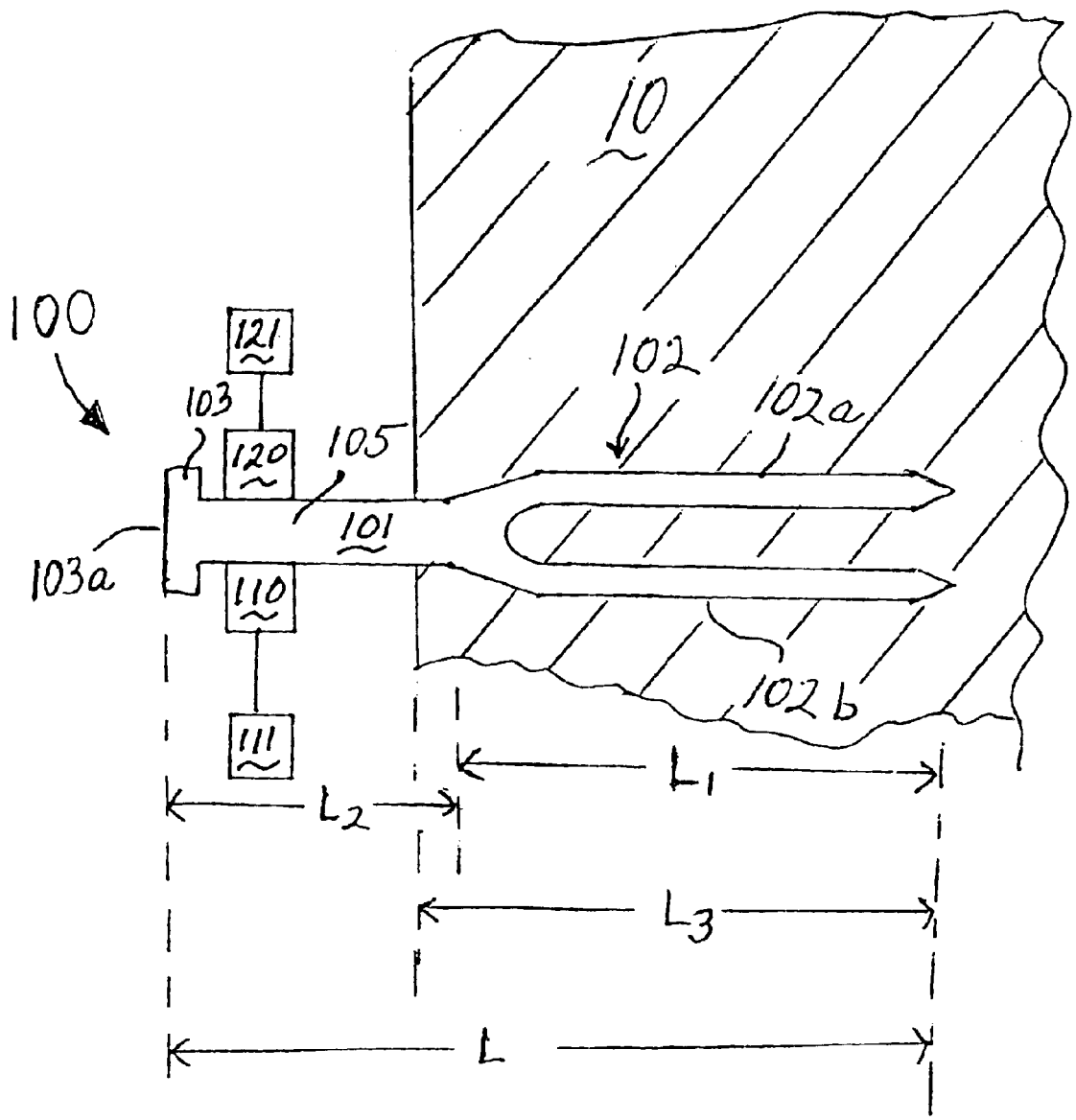
FIG. 1 is a schematic diagram of an embodiment of the apparatus of the invention applied to a tree.

Referring now to FIG. 1, an example tree probe apparatus 100 of the present invention includes a unitary, monolithic vibrative member 101 having a shaft 105 with a distal wood-penetrating end portion 102 and a head portion 103 at the proximal end of shaft 105. The distal wood-penetrating end portion 102 includes at least one prong characterized by a resonance frequency of mechanical vibration. The tree probe apparatus 100 is shown embedded in tree 10. A piezoelectric first transducer 110 is attached to the vibrative member 101 to cause it to vibrate at about the resonant frequency of the wood-penetrating end portion 102. An accelerometer 120 detects the amplitude of the vibrations of the tree probe at selected frequencies.

Figure 2:
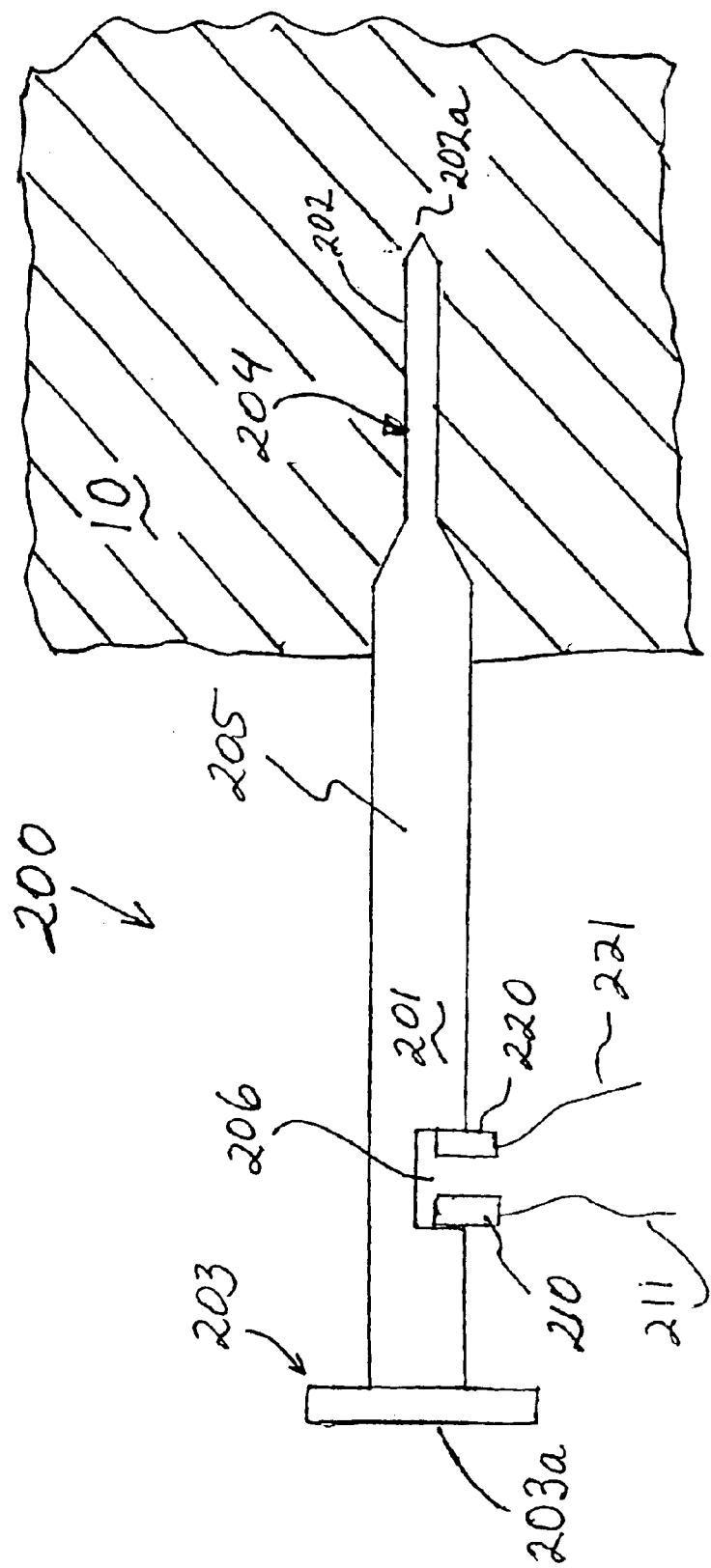
FIG. 2 is an alternative embodiment of the apparatus of the invention.

More particularly, the tree probe longitudinal vibrative member 101 is fabricated from a metal such as, for example, steel (e.g., carbon steel, stainless steel or other steel alloys), aluminum, non-ferrous alloys or any other suitable material (e.g., ceramic, plastic, etc.). The wood-penetrating end portion can have one or more prongs, each preferably having a tapered end terminating in a sharp point to facilitate the penetration of wood. In the event that a single prong is employed (as shown in FIG. 2) the prong can be threaded to facilitate screwing the tree probe into the wood of the tree.

As shown in FIG. 1, the tree probe 100 can include two spaced apart parallel prongs 102a and 102b at the distal wood-penetrating end. The prongs 102a and 102b are preferably constructed so as to have different resonance frequencies. A head-portion 103 has a proximal facing stop surface 103a which can be hammered to drive the tree probe 100 into the tree.

First transducer 110 is attached to the vibrative member 101 and applies vibrational energy to the tree probe 100 at or close to the resonant frequency of the prong(s) of the tree probe 100. Generally, the transducer 110 is piezoelectric in operation and converts electrical energy to mechanical energy. Piezoelectric stacks for use as transducer 110 are known. Suitable piezoelectric materials include, but are not limited to, quartz and piezoelectric ceramics such as, for example, barium titanate. Quartz has a high Q value but is more brittle. Barium titanate has high resistance to mechanical vibration and shock, as well as good chemical resistance. The size of transducer 110 can vary widely, e.g., the size can be relatively small, i.e., less than about 10 mm on a side and less than about 1 mm thick, and can be in the form of various shapes, e.g., rectangular, cylindrical, or annular shapes. Transducer 100 can be tunably driven by a variable frequency square wave or sine wave alternating current generator 111 or a resonant circuit preset to the resonant frequency of the one or more prongs 102a/102b. Such circuits are known in the art. Various transducers are known in the art and are commercially available. One such transducer suitable for use in the present invention as the first transducer is available under the designation/model number AE0203 D04 from Thor Labs.

An accelerometer 120 is attached to the vibrative member 101 of the tree probe to detect the vibrations and produce an electric signal proportional to the amplitude of the vibrations, which is analyzed by a Q meter 121 or is otherwise frequency scanned to provide amplitude data across a frequency spectrum which includes the resonant frequency of the prong. For example, by plotting the amplitude of the vibrations across a frequency spectrum one can obtain a characteristic curve from which the resonance bandwidth can be measured. The Q value can be determined by calculating the ratio between the resonant frequency and the bandwidth. Once the Q value is obtained for a particular tree it can be compared with Q values known for trees of various ages. For example, trees of known ages (determined, for example, by core sampling) can be tested to determine their Q values. A relationship between Q value and tree age for a type of tree (e.g., pine, oak, maple, etc.) can then be determined and recorded in the form of a chart, graph, or empirically derived mathematical formula. The Q value of a target tree of the same type can then be used to determine the age of the tree in accordance with the predetermined relationship.

The apparatus described herein is adapted for portability and use in the field. Generally, the tree probe 100 can have an overall length L ranging from about 75 mm to about 200 mm, and a diameter ranging from about 3 mm to about 15 mm, and preferably from about 5 mm to about 10 mm. The length $L_1$ of the prong(s) can typically range from about 5 mm to about 50 mm. The length $L_2$ of the shaft 105 typically can range from about 15 mm to about 150 mm. The shaft 105 has its own resonance and the dimensions of the shaft should be selected such that the shaft resonance does not overlap the resonance of the prong(s). The distance of penetration $L_3$ into the tree is limited to the distance between the sharp points of prongs 102a and 102b the position of the transducer 110 or accelerometer 120, which can typically range from about 5 mm to about 100 mm. These ranges are given for purpose of exemplification, and distances outside of these ranges can be used when appropriate. The tree probe 100 is inserted into a tree, e.g., by hammering the wood penetrating end of the vibrative member into the trunk of the tree. The transducers 110 and 120 are then attached to the side of vibrative member 101 of the tree probe and vibration of the tree probe is induced through transducer 110. The vibrations are then picked up by accelerometer 120 and the Q value is calculated as mentioned above. If the tree meets the appropriate criterion for harvest it can be cut for lumber. If it does not, the tree can be left to remain standing. In this manner, the tree can further grow and mature with minimal damage caused by the testing procedure and apparatus.

Referring now to FIG. 2 another embodiment 200 of the tree probe having only a single prong is illustrated. Tree probe 200 includes a unitary monolithic vibrative body member 201 having a cylindrical shaft 205 and a wood-penetrating end portion 204 extending distally from the shaft 205. A prong 202 of the wood penetrating end portion 204 includes a sharp distal point 202a. A head 203 has a proximal facing stop surface 203a which can be hammered to drive the prong 202 into the wood of the tree 10. Alternatively, the prong 202 can be threaded and head 203 can have a multisided (e.g. hexagonal) periphery to facilitate grasping by a wrench. A piezoelectric stack 210 is attached to a wall surface in a recess 206 in the shaft 205. An accelerometer 220 is attached to another wall surface in the recess 206 of the shaft 205. The piezoelectric stack 210 is electrically attached by wire(s) 211 to a means (not shown) for electrical excitation at a predetermined frequency. The accelerometer 220 is electrically attached by wire(s) 221 to means for converting the electrical signal of the accelerometer into data for calculating a quality factor.

Various features of the invention are shown by the non-limiting example set forth below.

EXAMPLE

This example presents calculations illustrating the effects of damping on a tree probe having a single prong such as that depicted in FIG. 2. The fundamental resonance frequency $f_n$ of the prong depends upon the spring constant k and the mass of material M. For a cantilevered rod the fundamental frequency is estimated by the following formula II:

$$f_n = \frac{n}{2\pi}\sqrt{\frac{k}{M}} = \frac{n}{2\pi}\sqrt{\frac{3\pi r^4 E}{4L^3\left(m_c + 0.24\frac{\pi r^2 L}{\rho}\right)}}, \quad (II)$$

wherein E is the elastic modulus, $m^c$ is the mass of the tip, r is the radius of the rod, L is the length of the rod and Δ is the density of the material The proposed tree probe for this example is fabricated from steel having an elastic modulus of $2.1 \times 10^{11}$ N/m² and a density of 7.65 g/cm³. The single prong (e.g., prong 202) is a cantilevered rod, having a diameter of 3.175 mm and a length of 15 mm. Using the dimensions and values given above the fundamental frequency of the proposed tree probe is calculated to be 10.4 kHz.

The damping effect of the tree fibers on the vibration amplitude of an implanted tree probe as a function of frequency f can be illustrated by the following formula III:

$$X(f,\zeta) = \frac{1}{\sqrt{\left(1-\frac{f^2}{f_n^2}\right)^2 + \left(\frac{2\zeta f}{f_n}\right)^2}}. \quad (III)$$

wherein $X_{(f,\zeta)}$ is the amplitude at frequency f, $\zeta$ is the damping coefficient, and $f_n$ is the calculated resonant frequency of the prong, e.g., 10.4 kHz.

Figure 3:
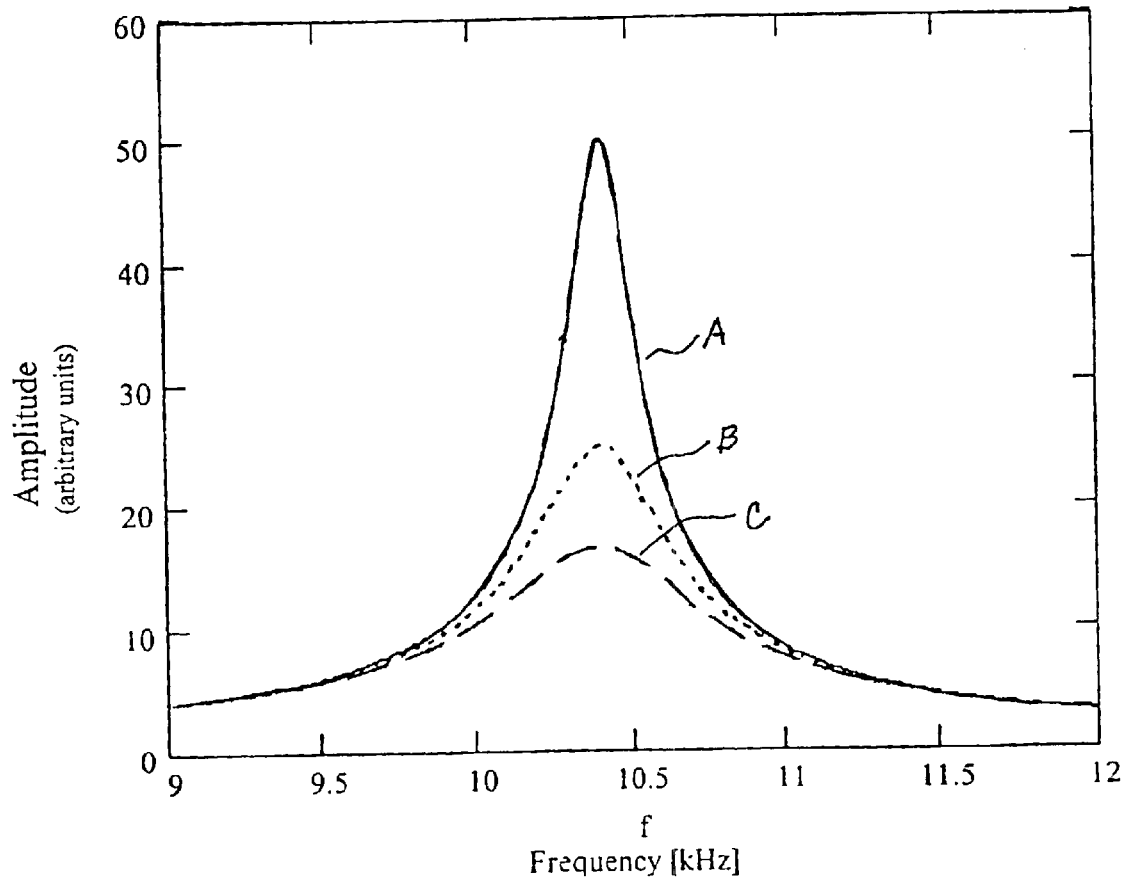
FIG. 3 is a graph of resonance patterns.

Referring now to FIG. 3, a graph illustrates calculated vibration amplitudes for the tree probe for three damping coefficients across a frequency spectrum. The amplitudes are in arbitrary units. Plot A depicts the amplitude variation for a damping coefficient of 0.01. The amplitude at resonance is 50 units. The corresponding Q value for plot A is calculated to be 29. Plot B depicts the amplitude variation for a damping coefficient of 0.02. The amplitude at resonance is 25 units. The corresponding Q value for plot B is calculated to be 14.6. Plot C depicts the amplitude variation for a damping coefficient of 0.03. The amplitude at resonance is 16.67 units. The corresponding Q value for plot C is calculated to be 9.54.

This Example shows how Q values relate to damping effects upon a resonant tree probe. Determination of the Q value can provide an indication of the tree maturity wherein the damping effects on the tree probe vibrations caused by the viscoelastic properties of the tree wood vary with the age of the tree.

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A method for selecting a tree according to a predetermined criterion, comprising the steps of:
   a) embedding a vibrative member in the tree, the embedded vibrative member having mechanical vibration resonance properties, including a resonance frequency and a resonance bandwidth;
   b) mechanically vibrating the vibrative member at or near the vibrative member resonance frequency;
   c) determining the resonance properties of the vibrative member, including the vibrative member resonance frequency and bandwidth;
   d) calculating an observed quality factor of the vibrative member based on the determined vibrative member resonance frequency and bandwidth; and,
   e) comparing the observed quality factor with a predetermined relationship between the quality factor and the tree selection criterion.

2. The method of claim 1 wherein the vibrative member has a wood-penetrating end portion characterized by the resonance frequency of mechanical vibration.

3. The method of claim 2 wherein the step of embedding the vibrative member to the tree comprises embedding the wood-penetrating end portion of the vibrative member into a trunk portion of the tree.

4. The method of claim 2 wherein the vibrative member is fabricated from a metal selected from the group consisting of stainless steel, steel alloys, aluminum and non-ferrous alloys.

5. The method of claim 2 wherein the vibrative member is fabricated from a material selected from the group consisting of ceramic and plastic.

6. The method of claim 1 wherein the tree selection criterion is dependent upon the maturity of the tree.

7. The method of claim 2 wherein the wood-penetrating end portion includes at least one prong.

8. The method of claim 2 wherein the wood penetrating end portion includes two prongs.

9. The method of claim 8 wherein the two prongs are each characterized by a different resonance frequency.

10. A tree probe comprising:
    a) a vibrative member having a wood-penetrating end portion characterized by at least one resonance frequency of mechanical vibration;
    b) means for mechanically vibrating the vibrative member, when the end portion thereof is embedded in a tree, at about the resonance frequency of the wood-penetration end portion; and,
    c) means for measuring vibration amplitude of the embedded vibrative member across a frequency range sufficient to include
       (i) the at least one resonance frequency, and
       (ii) a resonance bandwith of the embedded vibrative member, so as to determine a characteristic Q value thereof.

11. The tree probe of claim 10 wherein the wood penetrating end portion includes at least one prong.

12. The tree probe of claim 10 wherein the wood penetrating end portion includes two prongs.

13. The tree probe of claim 12 wherein the two prongs are each characterized by a different resonance frequency.

14. The tree probe of claim 10 wherein the vibrative member is fabricated from a metal selected from the group consisting of stainless steel, steel alloys, aluminum and non-ferrous alloys.

15. The method of claim 10 wherein the vibrative member is fabricated from a material selected from the group consisting of ceramic and plastic.

16. The tree probe of claim 14 wherein the vibrative member is a unitary single piece member.

17. The tree probe of claim 15 wherein the vibrative member is a unitary single piece member.

18. The tree probe of claim 16 wherein the means for vibrating the vibrative member comprises a piezoelectric transducer attached to the vibrative member and means for supplying the piezoelectric transducer with an alternating current at about the resonance frequency of the wood penetration end portion of the vibrative member.

19. The tree probe of claim 18 wherein the means for supplying an alternating current includes a tunable sine wave or square wave generator.

20. The tree probe of claim 10 wherein the means for measuring vibration amplitude includes an accelerometer attached to the vibrative member.

21. The tree probe of claim 10 wherein the means for vibrating the vibrative member comprises a piezoelectric transducer attached to the vibrative member and means for supplying the piezoelectric transducer with an alternating current at about the resonance frequency of the wood penetration end portion of the vibrative member and wherein the means for measuring vibration amplitude includes an accelerometer attached to the vibrative member.

* * * * *

UNITED STATES PATENT AND TRADEMARK OFFICE
CERTIFICATE OF CORRECTION

PATENT NO. : 6,829,938 B2
DATED : December 14, 2004
INVENTOR(S) : David W. Blodgett It is certified that error appears in the above-identified patent and that said Letters Patent is hereby corrected as shown below:

Column 6,
Line 1, delete "16" and insert therefor -- 10 --

Signed and Sealed this

Fourteenth Day of June, 2005

JON W. DUDAS
*Director of the United States Patent and Trademark Office*